United States Patent [19]

Auth et al.

[11] 4,126,136
[45] Nov. 21, 1978

[54] PHOTOCOAGULATING SCALPEL SYSTEM

[75] Inventors: David C. Auth, Bellevue; Robert F. Rushmer, Seattle, both of Wash.

[73] Assignee: Research Corporation, New York, N.Y.

[21] Appl. No.: 656,709

[22] Filed: Feb. 9, 1976

[51] Int. Cl.² ............................................. A61B 17/36
[52] U.S. Cl. ................... 128/303.1; 128/305; 219/121 L; 331/DIG. 1
[58] Field of Search ............ 128/303.1, 305, 395, 128/325, 303.14, 303.17, 303 R, DIG. 22, 396–398; 331/DIG. 1; 350/96 B, 96 R; 219/121 L, 121 LM

[56] References Cited

U.S. PATENT DOCUMENTS

| | | | |
|---|---|---|---|
| 3,283,124 | 11/1966 | Kawecki | 219/85 X |
| 3,467,098 | 9/1969 | Ayres | 128/303.1 |
| 3,538,919 | 4/1967 | Meyer | 219/349 X |
| 3,769,963 | 11/1973 | Goldman et al. | 128/303.1 X |
| 3,826,263 | 7/1974 | Cage et al. | 128/303.1 |

*Primary Examiner*—Robert W. Michell
*Assistant Examiner*—Michael H. Thaler
*Attorney, Agent, or Firm*—Seed, Berry, Vernon & Baynham

[57] ABSTRACT

A Photocoagulating scalpel system including a scalpel having a sharp, transparent blade for forming an incision, and a laser optically coupled to the blade for coagulating blood adjacent the incision. Laser radiation is transported to the blade through a low-loss fiberoptic waveguide. The radiation propagates through the waveguide and blade by means of multimode optical waveguide propagation wherein each mode has a discrete angle of incidence with respect to the blade surface. As the radiation reaches the beveled cutting edge of the blade, the angle of the blade surface changes causing the radiation to be emitted from the blade because the incident angles of individual modes fall below the critical internal reflection angle of the blade. Radiation leakage is further increased by the presence of blood on the blade surface which increases the critical internal reflection angle of the blade. Higher order modes having angles of incidence less than the critical internal reflection angles of the waveguide and blade are restricted so that radiation does not leak from the waveguide or blade before reaching the cutting edge. The laser radiation is preferably from an argon laser since its radiation is at a wavelength which is readily absorbed by red hemoglobin while being reflected by white tissue so that the radiation coagulates blood without causing extensive necrosis of the incised tissue. A power control on the handle of the scalpel allows the surgeon to adjust the intensity of the radiation as required depending upon the quantity of blood to be coagulated.

20 Claims, 7 Drawing Figures

FIG. 5
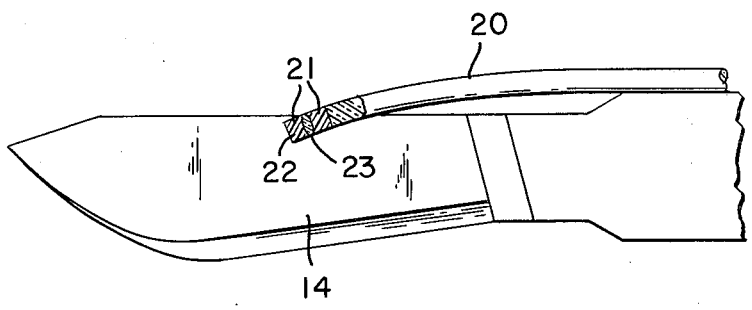
FIG. 6
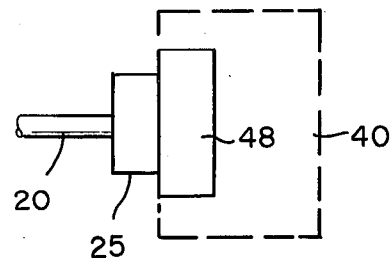
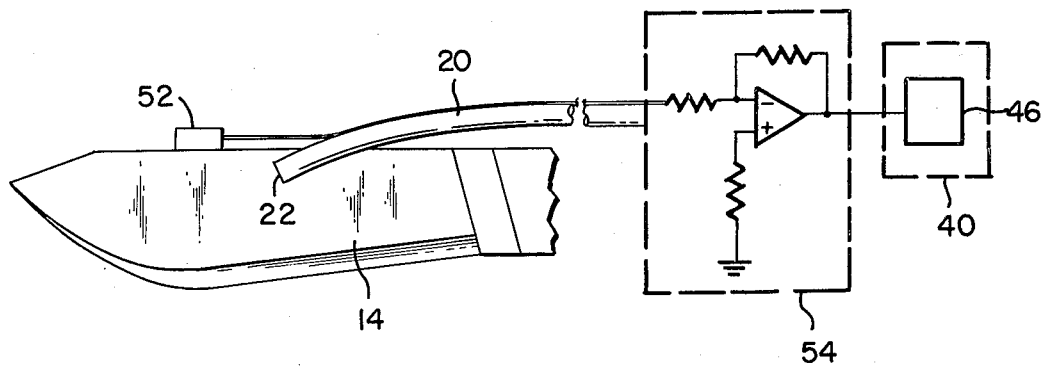
FIG. 7

PHOTOCOAGULATING SCALPEL SYSTEM

The invention described herein was made in the course of work under a grant or award from the Department of Health, Education and Welfare.

BACKGROUND OF THE INVENTION

1. Field of the Invention

This invention relates to surgical instruments and, more particularly, to a cold scalpel having a sharp edge for forming an incision, and means for irradiating tissue adjacent the cutting edge with laser radiation to provide rapid hemostasis.

2. Description of the Prior Art

A significant problem associated with surgical incisions is the control of bleeding. The problem is particularly acute for surgical removal of burn wound eschar and in surgery of highly vascularized organs such as the liver.

An important factor in the development of burn wound sepsis is the dead tissue of deeply burned areas which completely lose their resistance to invading bacteria. It has long been recognized that prompt, safe removal of the dead tissue is desirable, and attempts to do this by chemical and surgical means have been made. Only surgical removal has been carried out effectively, but with the attendant drawback of creating large blood losses necessitating extensive transfusions. Therefore, the early surgical excision of deep burns is generally limited to patients with moderate sized burns. Early eschar excision is also desirable to promote more rapid wound cover with autograft or homograft. In summary, earlier grafting should markedly decrease the incidence of bacterial wound sepsis, diminish the hypermetabolic response of the severely-burned patient, result in a shortened hospital admission and allow improved functional and cosmetic results.

Similar problems are associated with surgery on highly vascularized organs. Massive hemorrhage is sometimes a complication from small resections or even biopsies of the liver.

The use of focused laser radiation to incise and coagulate tissue has been widely considered, although such techniques have not been altogether satisfactory. Focused laser radiation forms incisions at a much slower rate than the conventional cold scalpel and, since the radiation must be absorbed by the incised tissue in order to create the incision, thermal necrosis to viable cells in the dermis is inevitable which appears responsible for inhibited epithelialization and contraction.

Another surgical device which attempts to simultaneously incise and coagulate tissue is the diathermy scalpel which utilizes high-frequency electrical current for hemostatic incisions. The principal disadvantages of this device, as with the use of focused laser radiation, is its slow speed and its tendency to cause thermal necrosis of viable cells adjacent the incision. Furthermore, there may be some tendency for the diathermy electrode to adhere to highly-vascularized organs since removal of an electrocoagulating electrode from the cut surface of a liver has, in some cases, reactivated bleeding.

Hemostatic incisions have also been attempted using a plasma scalpel in which a stream of high-temperature gases are directed at the tissue surface in order to form the incision and coagulate tissue adjacent the incision. Plasma scalpels exhibit the same disadvantages associated with focused laser radiation or the diathermy scalpel, namely slow excision rates and thermal necrosis. Furthermore, plasma gas embolization has been reported following surgery with the plasma scalpel.

SUMMARY OF THE INVENTION

The primary object of this invention is to prevent blood loss during surgery, particularly losses resulting from excision of burned wounds or surgery on highly-vascularized organs.

It is another object of this invention to provide a photocoagulating scalpel system which causes rapid hemostasis while limiting necrosis of incised tissue.

It is still another object of the invention to provide a photocoagulating scalpel system which cuts tissue with a speed comparable to conventional, non-coagulating scalpels.

It is a further object of the invention to provide a photocoagulating scalpel system which facilitates rapid healing of the incision and which has no adverse biological affects such as a tendency to cause embolization.

These and other objects of the invention are provided by a photocoagulating scalpel system including a blade having a cutting edge for forming an incision, and means for irradiating the cutting edge with laser radiation to coagulate blood emitted from the incised tissue. The blade preferably is transparent, with the radiation coupled from a laser to the blade by a fiber-optic waveguide, but external radiation sources directed at the cutting edge may also be employed. In the preferred embodiment the laser radiation propagates to the cutting edge by means of multimode optical waveguide propagation with higher order modes restricted to prevent premature leakage of radiation from the waveguide and blade.

BRIEF DESCRIPTION OF THE DRAWINGS

FIG. 5 is a schematic of the photocoagulating scalpel including a low-loss, index matching medium and an optical element between the blade and waveguide.

FIG. 6 is a schematic illustrating the use of an optical element positioned between the laser unit and waveguide.

FIG. 7 is a schematic illustrating an alternative embodiment of a power control system for the laser unit.

DETAILED DESCRIPTION OF THE DRAWINGS

Figure 1:
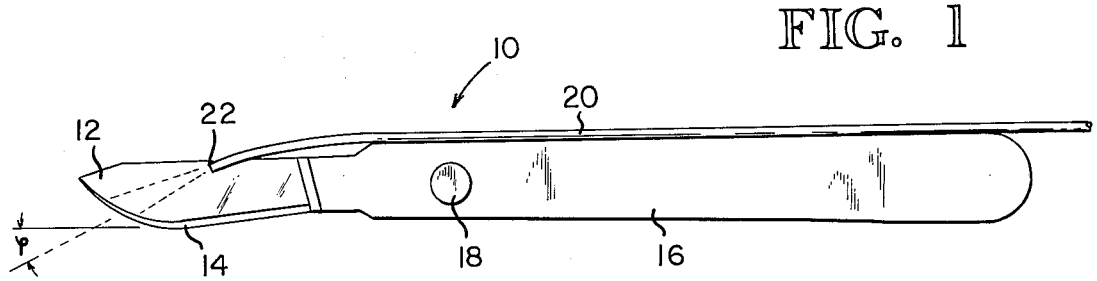
FIG. 1 is a side elevational view of the photocoagulating scalpel showing a transparent blade mounted on a handle with a fiberoptic waveguide delivering laser radiation to the blade.

The photocoagulating scalpel 10, as illustrated in FIG. 1, includes a transparent blade 12 having a sharp cutting edge 14. The blade 12 is mounted at the end of a conventionally-shaped scalpel handle 16 which contains a pressure-sensitive control 18 for adjusting the intensity of the laser radiation delivered to the blade 12. A fiberoptic waveguide 20 is optically coupled at one end to the blade so that laser radiation is injected into the transparent blade and then propagates to the cutting edge 14 where it is emitted from the blade.

The blade 12 may be formed by a variety of transparent materials, but synthetic sapphire is preferred since it is very hard and has a low optical absorption coefficient. In addition, synthetic sapphire is readily available at moderate cost. In one operational embodiment of the photocoagulating scalpel, the blade 12 was fabricated from a conventional, synthetic sapphire laser window (not shown) as sold by the Adolf Meller Company of Providence, R.I. The blade 12 is cut from the window, and the cutting edge 14 is formed by placing the blade against a grinding wheel. In order to prevent the grinding wheel from chipping or gouging the blade 12 during the formation of the cutting edge 14, blade deflection responsive to forces exerted by the grinding wheel must be prevented. One suitable technique involves flushly mounting the blade on a rigid backing plate (not shown) and forming the cutting edge by grinding both the blade 12 and backing plate. The backing plate is then removed after the cutting edge 14 has been formed on the blade 12.

The fiberoptic waveguide 20 which transports laser radiation to the blade 12, is flexible, light in weight and relatively rugged, particularly when encased in polyethelene tubing. Because of the high power density of the laser radiation, the waveguide must have low-loss characteristics in order to avoid destruction of the fiber. One type of optical waveguide which may be advantageously used is a step index, cylindrical quartz-glass fiber which is available from the Corning Glass Company. The quartz fiber is encapsulated in a laminated sheath of non-toxic polyethelene which may also contain leads (not shown) connected to the power control 18. The coupling of the waveguide 20 to the blade 12 requires a low-loss medium capable of withstanding the very high power densities at the exit point of the waveguide 20. A variety of coupling schemes are possible. A butt joint using epoxy, cyanoacrylate or resin cement as a low-loss bonding agent 21 as illustrated in FIG. 5. provides mechanical strength as well as optical transparency. The bonding agent 21 preferably has an index of refraction intermediate the indexes of refraction of the blade 12 and waveguide 20 in order to minimize reflection of the incident radiation from the blade 12. Alternatively, an index matching fluid or air coupling may be utilized with mechanical strength provided by a surrounding collar of cement. In general, the waveguide 20 should meet the blade 12 perpendicularly in order to provide optimum coupling. Various techniques for inclining the fiber waveguide to the blade axis can be employed. For example, as illustrated in FIG. 1, a V-shaped notch 22 can be formed at the top of the blade 12 for receiving the end of the waveguide 20. The injection angle $\phi$, i.e. the angle between the illuminating cone axis and the blade axis, may be varied to provide optimum results as explained hereinafter.

The handle 16, to which the blade 12 is secured, is of conventional shape and materials. The forward portion of the handle 16 includes a pressure-sensitive power control 18 which may be a variable resistor or variable capacitor. Leads (not shown) are connected to the control 18 and are preferably routed through a jacket enclosing the waveguide 20.

Figure 2:
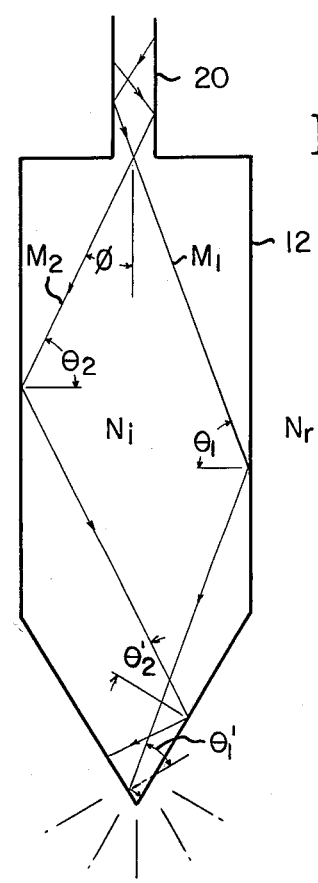
FIG. 2 is a schematic illustrating the propagation path of two modes of laser radiation through the blade of FIG. 1.

A schematic illustrating the manner in which the laser radiation propagates to the cutting edge is shown in FIG. 2. When a ray of light strikes an interface between substances having different indexes of refraction, the ray is refracted or bent. The angle of refraction $\theta_r$ is defined by Snell's law as being arcsin $N_i/N_r$ Sin $\theta_i$ where $\theta_i$ is the angle of incidence, and $N_i$ and $N_r$ (FIG. 2) are the indexes of refraction in the first and second mediums, respectively. When the angle of refraction ($\theta_r$) reaches 90° the angle of incidence ($\theta_i$) is equal to the "critical angle". For angles of incidence in excess of the critical angle, all of the light is internally reflected. The critical angle $\theta_c$ is equal to arcsin $N_r/N_i$. As illustrated in FIG. 2, a ray of light $M_1$ injected into the blade 12 strikes the blade surface at an angle $\theta_1$ which is greater than the critical angle $\theta_c$. Consequently, all of the incident radiation is internally reflected. As the ray $M_1$ propagates toward the tapered cutting edge 14, it continues to be internally reflected from the parallel surfaces of the blade 12, but at the cutting edge 14, the angle of incidence $\theta_{1'}$ is less than the critical angle $\theta_c$ and part of the incident radiation is emitted from the blade 12. Similarly, the ray of light $M_2$ has an angle of incidence $\theta_2$ at the upper portion of the blade which is greater than the critical angle $\theta_c$ so that all of the incident radiation is internally reflected. When the ray strikes the surface of the beveled cutting edge 14, its angle of incidence $\theta_{2'}$ is less than the critical angle and some of the incident radiation is emitted from the blade 12. It should be emphasized that even though the incident angle is less than the critical angle, only a portion of incident radiation is emitted from the blade since part of the incident radiation will still be reflected.

In practice, the laser radiation injected into the blade 12 from the fiberoptic waveguide 20 has a relatively narrow illumination cone. The cone is defined as having a numerical aperture equal to sin $\phi$ where $\phi$ is the half angle of the angle of the cone divergence. The numerical aperture of the illuminating cone is restricted so that the minimum angle of incidence of the light rays is set above the critical internal reflection angle so that all of the radiation is internally reflected in the parallel sided portion of the blade 12.

For clarity of illustration, only two rays or modes $M_1, M_2$ are illustrated in FIG. 2. In actuality, hundreds of such mode exist, each having a discrete propagation angle or angle of incidence to the blade surface. Only a portion of the possible modes are excited in the waveguide 20 and blade 12 since individual modes interfere with each other to form null points across the width of the blade which are similar to the null points of standing waves in a transmission line. Only those modes which are capable of providing the proper boundary conditions, i.e. zero intensity at the blade surfaces, are excited in the waveguide and blade. Furthermore, the selection of which modes are excited in the blade is affected by which modes are excited in the waveguide. The lowest order modes have the largest angle of incidence and, hence, are the last to be emitted from the blade surface. Higher order modes have a lower angle of incidence and are more easily emitted from the blade. For example, one wavelength of argon laser radiation may propagate through a 0.5mm. thick sapphire blade by approximately 2,000 discrete modes. Yet only about the lowest 1,600 modes have an angle of incidence greater than the critical internal reflection angle where air is the external medium. In order to prevent premature radiation leakage, propagation modes having an angle of incidence less than the critical angle are restricted by restricting the numerical aperture at which the radiation is injected into the blade. This numerical aperture restriction can be accomplished by placing an optical element 23 between the fiberoptic waveguide 20 and blade 12 as illustrated in FIG. 5 to redistribute the intensity profile of excited waveguide modes in order to achieve a particular rate and distribution of leakage at the cutting edge 14. These optical elements 23 may include such devices as lenses, prisms, gratings, polarizers, etc., which manipulate the relative spectral weighing of the injected radiation. Alternatively, the numerical aperture at which the laser radiation is injected into the waveguide may be restricted since restricting the modes which are excited in the waveguide 20 restricts which modes can be excited in the blade 12. One example of this alternative embodiment is illustrated in FIG. 6. A conventional optical element 25 such as a lens, prism, grating, etc. is placed between the coupling optics 48 of the laser unit 40 and the waveguide 20. As the laser radiation propagates in the tapered zone near the cutting edge 14, it partially leaks out of the blade 12 as mode conversion occurs and individual modes fall below the critical internal reflection angle. The leakage will be enhanced by the presence of blood on the blade surface since the optical index of refraction of blood is substantially higher than air and, hence, increases the magnitude of the critical angle.

The rate and position of the radiation leakage can can also be modified by adjusting the blade taper angle and profile, as well as the index of refraction of the blade. For example, a sapphire blade has a critical angle for total internal reflection with air as the external medium of about 35°. When the sapphire blade is emerged in water, the critical angle increases to about 49°. Higher order modes excited in the blade having angles of incidence between 35° and 49° would be emitted from the blade if the blade were immersed in water or blood, but would propagate without significant loss if the blade 12 were surrounded by air. Low order modes having angles of incidence greater than 49° would be totally internally reflected even if the blade were immersed in water. However, as the modes propagate and sustain multiple reflections in the tapered zone of the cutting edge 14, mode conversion occurs and the angle of incidence of the modes with the blade surface varies. Thus, those modes or rays having angles of incidence greater than 49° in the portion of the blade having parallel sides, would experience angular shifts in the tapered zone of the cutting edge and begin to experience partial leakage from the blade as their incident angles drop below the critical angle for the particular external medium. It is apparent that a particular leakage profile can be obtained by proper arrangement of the modes which are excited at the point of injection. The injection angle $\phi$ (FIG. 1) may also be adjusted to vary the characteristics of the laser radiation emitted from the blade 12. However, if the injection angle $\phi$ is too small, the injected radiation is reflected from the cutting edge 14 since its angle of incidence may become greater than the critical internal reflection angle at the cutting edge 14 of the blade 12.

Figure 4:
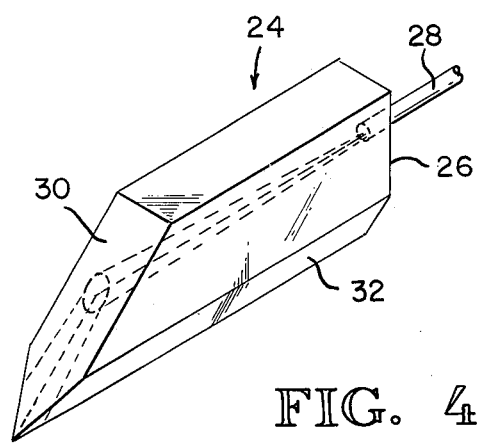
FIG. 4 is a side elevational view of an alternative embodiment of the scalpel blade.

An alternative embodiment of a transparent blade is illustrated in FIG. 4. Laser radiation is injected into the blade 24 at an end face 26 through a fiberoptic waveguide 28. The radiation propagates by means of multimode waveguide propagation along the longitudinal axis of the blade and is reflected from an angled end wall 30 toward the cutting edge 32 of the blade 24. If desired, the end wall 30 may be curved to provide a predetermined reflection pattern such as a relatively wide disbursement of the radiation.

If desired, the blades 12,24 may be coated with commercially available substance to prevent blood from accumulating on the blade surface.

Figure 3:
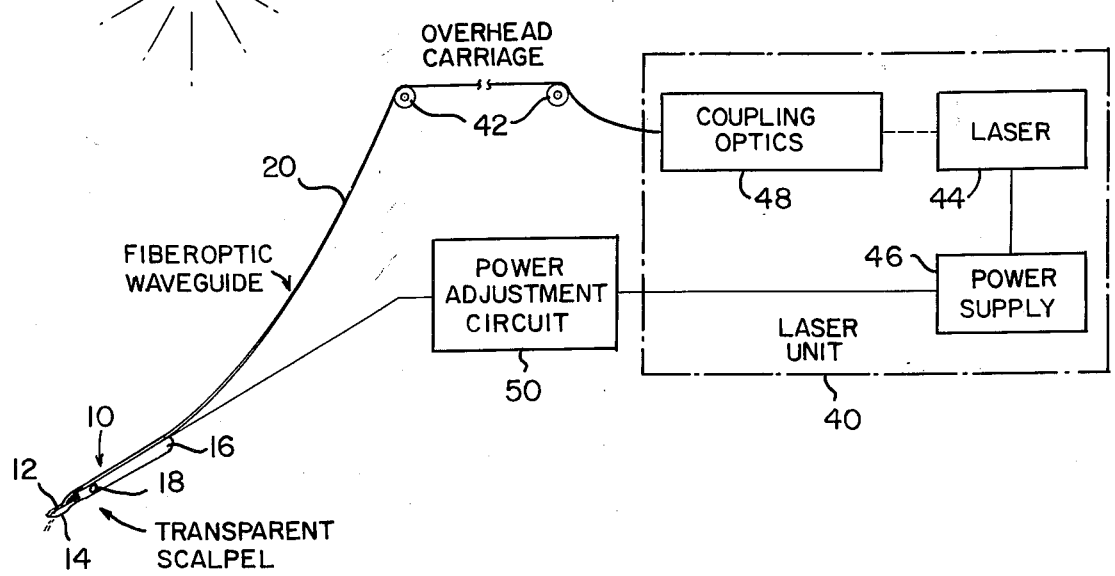
FIG. 3 is a schematic of the photocoagulating scalpel system.

A schematic of the overall system for the photocoagulating scalpel is illustrated in FIG. 3. The transparent blade 12 of the scalpel 10 is optically coupled to the fiberoptic waveguide 20 which extends to a laser unit 40. The waveguide 20 may be supported between the scalpel 10 and laser unit 40 by an overhead carriage 42 or support arm. The laser unit 40 includes a laser 44 connected to an adjustable power supply 46. Since the laser beam is generally substantially wider than the waveguide 20, coupling optics 48 are placed between the laser 44 and waveguide 20 to reduce the width of the laser beam to correspond to the width of the waveguide 20. The coupling optics 48 may also be used to adjust the characteristics of the laser radiation entering the waveguide 20 such as, for example, to restrict the numerical aperture of the radiation as previously explained.

The power supplied to the laser 44 by the power supply 46 may be controlled to adjust the intensity of the laser radiation from the laser 44 in order to ensure rapid coagulation without causing undue necrosis. For this purpose, a power adjustment system includes a pressure-sensitive power control 18 on the handle 16 which may be a commercially available pressure-sensitive resistor or capacitor. The power control 18 is connected by leads (not shown) to a power adjustment circuit 50 which converts the output of the control 18 to a voltage for modulating the power modulation input of the laser power supply 46. For example, the power adjustment circuit 50 may be a DC voltage source connected to the ends of a variable resistor with the resistor center tap connected to the power supply 46. Alternative power control systems may also be divised which automatically set the intensity of the laser radiation to an optimum value. One such system illustrated in FIG. 7 includes a sensor 52 for measuring the laser radiation internally reflected from the cutting edge 14 toward the waveguide 20. The optical sensor is preferably placed at the top portion of the blade 12. An excessive amount of internally reflected light indicates that laser radiation is of an intensity greater than can be absorbed by blood emanating from the incised tissues. The power control system provides a voltage to the power modulation input of the laser power supply which maintains the intensity of the internally reflected light relatively constant. This may be accomplished simply by connecting the output of the optical sensor to an inverting amplifier 54 which produces a voltage inversely proportional to the voltage at the output of the sensor. The output of the amplifier is connected to the power supply 46 of the laser unit 40 in the same manner as the power adjustment circuit 50 of FIG. 3.

In operation, laser radiation is delivered to the blade 12 of the scalpel 10 through the fiberoptic waveguide 20. The cutting edge 14 of the blade 12 forms an incision, and laser radiation emitted from the blade 12 adjacent the cutting edge 14 coagulates blood emanating from the incised tissues. By adjusting the pressure on the control element 18, the surgeon may control the amount of laser radiation delivered to the blade 12 depending upon the quantity of blood present which must be coagulated.

The laser unit 40 must be capable of producing laser radiation having an intensity sufficient to rapidly coagulate blood. A 20 watt continuous wave laser is considered adequate for this purpose. Although the invention should not be considered as being limited to any particular type of laser, an argon laser appears most desirable since its blue-green light is selectively absorbed by the red hemoglobin of blood, its radiation is visible, it can be transmitted through a flexible quartz waveguide with relatively low loss, and it is available in sufficiently high continuous powers to enable rapid coagulation. While the argon laser radiation is rapidly absorbed by red hemoglobin, it is only mildly absorbed by white tissue thereby reducing the amount of necrosis in the tissue surrounding the incision while providing adequate energy to the red hemoglobin to arrest bleeding. A commercially available laser unit having the characteristics described above is Model No. CR-18 of Coherent Radiation, Inc., of Palo Alto, Calif. This unit is a 20 watt argon laser having a power modulation input for adjusting the intensity of the laser radiation responsive to an applied voltage.

Although the use of a transparent blade optically coupled to a laser is the preferred embodiment, other systems for irradiating incised tissue adjacent the cutting edge of a cold scalpel may also be employed. For example, a sharp steel blade may be sandwiched between transparent plates optically coupled to a laser. The plates stop short of the cutting edge, but laser radiation emitted from the edges adjacent the cutting edge coagulates blood emanating from the incised tissues. Alternatively, a plurality of spaced apart optical waveguides coupled to a laser may be embedded in a sharp steel blade with the waveguides terminating at or near the blade cutting edge.

The photocoagulating scalpel system of the present invention can advantageously be used for relatively bloodless surgery without such disadvantages as tissue necrosis and slow operation associated with prior art devices, even for such problem surgery as burn wound removal and surgery on highly-vascularized organs such as the liver.

The embodiments of the invention in which a particular property or privilege is claimed are defined as follows:

1. A photocoagulating scalpel system comprising a scalpel having a blade with a sharp cutting edge, and laser means for coagulating blood including light transmitting means connected to said scalpel for conveying laser radiation to a location closely adjacent and exterior to said cutting edge such that while said blade forms incisions said laser radiation moves in correspondence with the movement of said blade thereby coagulating blood adjacent said cutting edge.

2. The photocoagulating scalpel system of claim 1 wherein said scalpel blade is transparent and said laser means includes a laser supplying sufficient power to coagulate blood, and a fiberoptic waveguide having one end optically coupled to said laser and the other end optically coupled to the blade of said scalpel such that radiation from said laser propagates through said waveguide and blade, and is emitted from said blade proximate said cutting edge.

3. The photocoagulating scalpel system of claim 2 wherein said laser radiation propagates through said waveguide and blade by means of multimode optical waveguide propagation wherein a plurality of modes each have a discrete propagation angle corresponding thereto such that the angles of incidence of higher order modes are smaller than the angles of incidence of lower order modes.

4. The photocoagulating scalpel system of claim 3 further including means for preventing excitation of higher order modes which have an angle of incidence smaller than the critical internal reflection angle of said waveguide and the portion of said blade away from said cutting edge such that said laser radiation is substantially prevented from leaking from said waveguide and blade before reaching said cutting edge.

5. The photocoagulating scalpel system of claim 4 wherein said means for preventing excitation of higher order modes includes means for limiting the numerical aperture of the laser radiation injected by said waveguide below a predetermined value.

6. The photocoagulating scalpel system of claim 5 wherein said means for limiting said numerical aperture includes an optical element placed at the interface between said waveguide and blade such that said laser radiation passes therethrough.

7. The photocoagulating scalpel system of claim 5 wherein said means for limiting said numerical aperture includes an optical element placed at the interface between said waveguide and laser such that said laser radiation passes therethrough.

8. The photocoagulating scalpel system of claim 3 further including an optical element placed at one end of said waveguide for redistributing excited modes thereby providing a predetermined rate and distribution of leakage from said blade.

9. The photocoagulating scalpel system of claim 2 wherein the taper of said cutting edge is adjusted to provide a predetermined rate and distribution of leakage from said blade.

10. The photocoagulating scalpel system of claim 2 wherein the injection angle at which said laser radiation is coupled to said blade is adjusted to provide a predetermined rate and distribution of leakage from said blade.

11. The photocoagulating scalpel system of claim 2 wherein the optical coupling is accomplished by placing a low-loss medium between said blade and said waveguide, said medium having an index of refraction adapted to provide index matching to increase the coupling between said waveguide and blade.

12. The photocoagulating scalpel system of claim 2 further including control means for adjusting the intensity of laser radiation delivered to said blade.

13. The photocoagulating scalpel system of claim 12 wherein said laser includes external power modulation means for adjusting the intensity of said laser radiation responsive to the signal at a power modulation input, and wherein said control means comprise an electrical control element mounted on said scalpel, and a control circuit connected to said control element and said power modulation input, said control circuit converting the output of said electrical control element to a signal for adjusting the intensity of said laser radiation in response thereto.

14. The photocoagulating scalpel system of claim 12 wherein said laser includes external power modulation means for adjusting the intensity of said laser radiation responsive to the signal at a power modulation input, and wherein said control means includes blood detector means connected to said power modulation input for sensing the quantity of blood adjacent to said cutting edge and providing an electrical control signal in response thereto such that the intensity of laser radiation delivered to said blade is proportional to the quantity of blood to be coagulated.

15. The photocoagulating scalpel system of claim 14 wherein said blood detector means includes light-sensing means for detecting the intensity of light internally reflected from said cutting edge toward said waveguide and for adjusting said control signal in response thereto such that the intensity of said internally reflected light is relatively constant.

16. The photocoagulating scalpel system of claim 2 wherein said blade is fabricated from a sheet of sapphire, and said cutting edge is formed by placing one edge of said sheet against a grinding wheel while preventing deflection of said edge responsive to forces exerted on said sheet by said grinding wheel.

17. The photocoagulating scalpel system of claim 2 wherein said transparent blade has a first end wall receiving said laser radiation along a line substantially parallel to the longitudinal axis of said blade, and wherein said blade has a second end wall at the opposite end of said blade from said first end wall which is disposed at an angle to said longitudinal axis such that said laser radiation is reflected by said second end wall toward said cutting edge.

18. The photocoagulating scalpel system of claim 17 wherein said second end wall of said blade is curved to disburse laser radiation incident on said second end wall.

19. The photocoagulating scalpel system of claim 1 wherein said laser radiation is at a wavelength chosen to provide selective absorption such that said radiation is absorbed more readily by red hemoglobin than by white tissues whereby the amount of necrosis in the tissue adjacent an incision is relatively slight while the coagulation of blood is relatively rapid.

20. A photocoagulating scalpel system comprising:
- a continuous-wave laser supplying laser radiation having an intensity controllable by a control signal at a power modulation input;
- a flexible, low-loss, fiberoptic waveguide having one end optically coupled to said laser such that radiation from said laser propagates through said waveguide by means of multimode optical wave guide propagation;
- a scalpel having a handle and a transparent blade with a relatively sharp cutting edge, said blade being optically coupled at the other end of said waveguide such that said laser radiation propagates toward said cutting edge by the use of multimode optical waveguide propagation;
- means for preventing modes from propagating into said blade having an angle of incidence less than the critical internal reflection angles of said waveguide and the portion of said blade away from said cutting edge such that said radiation propagates through said waveguide and blade and is emitted immediately adjacent said edge; and
- control means positioned on the handle of said scalpel and operatively associated with said laser for adjusting the intensity of radiation generated by said laser to correspond to the quantity of blood to be coagulated.

* * * * *